(12) United States Patent
Yamaya et al.

(10) Patent No.: US 9,029,790 B2
(45) Date of Patent: May 12, 2015

(54) METHOD AND SYSTEM FOR IMAGING USING NUCLEAR MEDICINE IMAGING APPARATUS, NUCLEAR MEDICINE IMAGING SYSTEM, AND RADIATION THERAPY CONTROL SYSTEM

(75) Inventors: Taiga Yamaya, Chiba (JP); Eiji Yoshida, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 282 days.

(21) Appl. No.: 13/638,745

(22) PCT Filed: Mar. 30, 2010

(86) PCT No.: PCT/JP2010/055733
§ 371 (c)(1),
(2), (4) Date: Oct. 18, 2012

(87) PCT Pub. No.: WO2011/121737
PCT Pub. Date: Oct. 6, 2011

(65) Prior Publication Data
US 2013/0037722 A1 Feb. 14, 2013

(51) Int. Cl.
*G01T 1/164* (2006.01)
*A61B 6/03* (2006.01)
*A61B 6/00* (2006.01)

(52) U.S. Cl.
CPC ............... *A61B 6/037* (2013.01); *A61B 6/5205* (2013.01)

(58) Field of Classification Search
CPC .............................. A61B 6/5205; A61B 5/037
See application file for complete search history.

(56) References Cited

U.S. PATENT DOCUMENTS

| 5,608,221 | A | 3/1997 | Bertelsen et al. |
| 2005/0253074 | A1 | 11/2005 | Jones et al. |
| 2008/0285828 | A1* | 11/2008 | Gagnon et al. ............... 382/131 |
| 2010/0128956 | A1* | 5/2010 | Yamaya et al. ............... 382/132 |

FOREIGN PATENT DOCUMENTS

| JP | B2-2535762 | 9/1996 |
| JP | B2-2550540 | 11/1996 |
| JP | A-9-5440 | 1/1997 |
| JP | B2-2811718 | 10/1998 |
| JP | A-2001-33556 | 2/2001 |
| JP | A-2007-537458 | 12/2007 |
| WO | WO 2008/129666 A1 | 10/2008 |
| WO | WO 2009/133628 A1 | 11/2009 |

OTHER PUBLICATIONS

International Preliminary Report on Patentability issued in International Patent Application No. PCT/JP2010/055733 dated Oct. 23, 2012.
Noda et al., "New Accelerator Facility for Carbon-Ion Cancer Therapy," *J. Radiant, Res.*, vol. 48, Suppl. A, 2007, pp. 43-54.

(Continued)

*Primary Examiner* — Constantine Hannaher
(74) *Attorney, Agent, or Firm* — Oliff PLC

(57) ABSTRACT

In imaging on the basis of list mode data of a list of radioactive count data detected by a nuclear medicine imaging apparatus for measuring radiation in a pulse mode, the processing from the measurement to imaging of radiation is accelerated substantially to the real time level by selecting the number of count data to be used for online imaging computations on the basis of the counting rate of radiation.

20 Claims, 13 Drawing Sheets

(56) References Cited

OTHER PUBLICATIONS

Yamaya et al., "A Proposal of an Open PET Geometry," *Physics in Medicine and Biology*, vol. 53, 2008, pp. 757-773.

Yamaguchi et al., Development of Patient Setup Verification System Using Parallel-Plane PET—Fundamental Study Using GEANT4 Simulation—, *Japanese Journal of Medical Physics*, vol. 29, No. 3, pp. 174-175. Sep. 2009.

Enghardt et al., "Charged Hadron Tumour Therapy Monitoring by Means of PET," *Nuclear Instruments & Methods in Physics Research*, Section A, vol. 525, 2004, pp. 284-288.

Nishio et al., "Dose-Volume Delivery Guided Proton Therapy Using Beam On-Line PET System," *Med. Phys.*, vol. 33, No. 11, Nov. 2006, pp. 4190-4197.

Hudson et al., "Accelerated Image Reconstruction Using Ordered-Subsets of Projection Data," *IEEE Transactions on Medical Imaging*, vol. 13, No. 4, Dec. 1994, pp. 601-609.

Nakayama et al., "Derivation and Implementation of Ordered Subsets Algorithms for List-Mode PET Data," *IEEE Nuclear Science Symposium Conference Record*, 2005, pp. 1950-1954.

Kinouchi et al., "Implementation of List-Mode PET Reconstruction Using GPU," *IEICE Technical Report*, vol. 109, No. 407, pp. 57-60 (with Abstract), Jan. 2010.

Yoshida et al., "Basic Investigation of Data Acquisition System for Next Generation PET Scanner," *Japanese Journal of Medical Physics*, vol. 23, No. 1, 2003, pp. 65-72 (with Abstract).

Sato et al., "(5) jPET-D4 Seigyo Sochi," *Jisedai PET Sochi Kaihatsu Kenkyu Hokokusho*, Heisei 16 nendo, NIRS-M-178, pp. 31-36, Mar. 2005.

International Search Report issued in International Patent Application No. PCT/JP2010/055733 dated Jul. 13, 2010 (with translation).

* cited by examiner

METHOD AND SYSTEM FOR IMAGING USING NUCLEAR MEDICINE IMAGING APPARATUS, NUCLEAR MEDICINE IMAGING SYSTEM, AND RADIATION THERAPY CONTROL SYSTEM

TECHNICAL FIELD

The present invention relates to methods and systems for imaging using nuclear medicine imaging apparatus which conduct radiation measurements in a pulse mode, nuclear medicine imaging systems, and radiation therapy control systems. More particularly, the invention relates to a method and a system for imaging using a nuclear medicine imaging apparatus, a nuclear medicine imaging system, and a radiation therapy control system, which are preferred for use with gamma cameras, positron cameras, single photon emission computed tomography (SPECT) device, positron emission tomography (PET) device or the like, and which are capable of accelerating the processing from the measurement to imaging of radiation substantially to a real time level so as to display or analyze images in real time.

BACKGROUND ART

The positron emission tomography (PET) has received attention as being effective for early diagnosis of cancer. The PET or an examination method has been used for examining the presence or level of diseases or for cancer diagnosis by giving a compound marked by a trace amount of a positron emission nuclide to the body and then detecting annihilation radiation emitted therefrom, thereby imaging a metabolic function such as glucose metabolism. In order to implement this examination method, the PET device has been brought into practical use.

The principle of the PET is as described below. Positrons emitted in the positron decay of a positron emission nuclide may disappear by annihilation in pairs with surrounding electrons so as to yield a pair of annihilation radiations at 511 keV, which are measured with a pair of radiation detectors on the basis of the principle of coincidence. This makes it possible to identify the position of presence of the nuclide on one line segment connecting between the pair of detectors (a line of response). The distribution of nuclides within the patient body can be known from the data obtained by measuring lines of response in various directions using the detectors disposed so as to surround the patient and observing PET images provided by an image reconstruction operation. The research and development of new PET medicines (probes) for diagnosis of cancer properties, typified by an oxygen state, have been actively conducted in addition to the research and development for providing improved device performances such as resolution.

Nuclear medicine imaging apparatus including the PET measure radiation in a pulse mode in which the radiation is measured (or counted) on every pulse.

On the other hand, the role of therapy for the cancer that is identified by diagnosis with the PET is also critical. As a method different from surgery or medication, there is available a radiation therapy in which an affected area is irradiated with radiation such as X-rays or gamma rays. In particular, the particle beam therapy in which a cancer portion is concentratedly irradiated with heavy particle beams or proton beams has gained great attention as a method which offers outstanding therapeutic effects and allows for irradiating affected areas with sharply focused beams. As a method for irradiation with particle beams, studies have been conducted on spot scanning irradiation for scanning a pencil beam across an affected area, e.g., to follow the shape thereof, in addition to the conventional Bolus irradiation for spreading the beam with which the affected area is irradiated so as to follow the shape thereof (Non-Patent Literature 1). Any of the studies above are conducted by providing precise control to the direction and dose of irradiation beams in accordance with the therapy plan which has been carefully computed on the basis of a separately captured X-ray CT image or the like. However, there is no denying the risk that a tumor would vary in shape in several weeks from the creation of a therapy plan to the practicing of the therapy, and there is no way for checking whether irradiations have been performed as planned, under current circumstances except for prognostic diagnosis after several weeks.

In this context, the applicants have tried integrating the therapy apparatus with the PET device so as to enable a therapy plan itself to be immediately modified on the basis of a PET image, whereby it has been aimed to achieve the positive radiation cancer therapy which is optimized for each patient and thus each tumor by performing irradiation while (1) directly observing the cancer, (2) observing the dose distribution, and also (3) observing the therapeutic effects. More specifically, as shown in FIG. 1, as a method for enabling three-dimensional PET imaging with a gap through which a therapeutic beam passes, the applicants have suggested the open PET device in which multi-ring detectors 22 and 24 divided into two in the direction of the body axis of a patient 8 (along the z axis in the figure) are spaced apart from each other and which has a physically opened field of view region (also referred to as the open field of view) (Patent Literature 1 and Non-Patent Literature 2). In the open field of view, an image is reconstructed from the lines of response between both the divided detector rings 22 and 24. The figure shows a bed 10, a bed base 12, a gantry cover 26, a radiating apparatus 30, and a therapeutic beam 32.

There have been available previous examples in which a counter (dual) gamma camera type PET device specialized in two-dimensional imaging was combined with a radiation therapy. (1) Concerning the irradiation while directly observing the cancer, studies have been conducted on a method of directly visualizing a tumor referring to not a conventional X-ray transmission image but a PET image in aligning the patient (Non-Patent Literature 3). Furthermore, (2) concerning the observation of the dose distribution, studies have been conducted on a method in which the PET medicine is not given, but in the irradiation with particle beams or X-ray, the annihilation radiation to be produced through the fragmentation reaction of an incident nucleus, the fragmentation reaction of a target nucleus (also referred to as the auto activation), or the photonuclear reaction is imaged on the basis of the principle of the PET (Non-Patent Literatures 4 and 5). Therapy monitoring is considered possible because the position of occurrence of the annihilation radiation is strongly correlated with the dose distribution of irradiation beams.

However, reviewing the processing from the measurement to imaging of radiation, it took several minutes to compute a reconstructed image. Thus, in any conventional methods, it was impossible to modify the therapy plan in synchronization with the therapy on the basis of the information obtained from the PET image and then control the irradiation beam. That is, to implement the beam control based on the feedback from the PET image, it is required to implement high-speed imaging nearly at a real-time level.

The image reconstruction technique is largely divided into the analytical image reconstruction technique which is typified by the filtered back-projection method, and the iterative image reconstruction technique which is typified by the maximum-likelihood expectation-maximization (ML-EM) method. The former can perform calculations quickly but there is a limit in improving image quality. The latter is known to be effective for improving image quality, but requires a long time for iterative computations; attention is being focused on a high-speed method, such as the OSEM method (Non-Patent Literature 6), in which data is divided into subsets (blocks) and then images are updated in blocks. In previous studies based on the same way of thinking as for the X-ray CT, the sinogram (the histogram data of measured counts) was divided into blocks, and thus the number of blocks was limited and the level of speed enhancement was far off the real-time level. On the other hand, the real time processing is impossible in the first place even if images can be reconstructed at sufficiently enhanced speeds because measured counts have to be integrated over time before the sinogram is obtained. However, for the PET, if images can be directly reconstructed from the list mode data (the list of data (count data) on each count of annihilation radiation), which is the source of sinogram, the aforementioned integration over time is not required and the number of blocks can be increased to a great extent. Thus, a significant enhancement in the speed of reconfiguration computations can be expected (Non-Patent Literature 7). This image reconstruction technique shows great promise for the possibility of providing a reconstructed image through only one computation (one-pass) without iterative computations.

CITATION LIST

Patent Literature

Patent Literature 1: International Patent Publication WO2009/133628 A1

Non-Patent Literature

Non-Patent Literature 1: Noda et al., J Radiat Res A 48 (Sup) p43 2007.
Non-Patent Literature 2: Taiga Yamaya, Taku Inaniwa, Shinichi Minohara, Eiji Yoshida, Naoko Inadama, Fumihiko Nishikido, Kengo Shibuya, Chih Fung Lam and Hideo Murayama, "A proposal of an open PET geometry," Phy. Med. Biol., 53, pp. 757-773, 2008.
Non-Patent Literature 3: Yamaguchi et al., Medical Physics, 29(3) p174 2009.
Non-Patent Literature 4: Enghardt et al., NIMA p284 2004.
Non-Patent Literature 5: Nishio et al., Med Phys p4190 2006.
Non-Patent Literature 6: Hudson and Larkin IEEE TMI p601 1994.
Non-Patent Literature 7: Nakayama and Kudo IEEE NSS-MIC M05-7 2005

However, the counting rate (the frequency of measurements of list mode data) expected in the PET device may fall within a wide range from $10^3$ counts/sec (auto activation for reduced doses) to $10^7$ counts/sec (the maximum value of measurements obtained by a typical PET probe). Accordingly, high counting rates require long time to transfer data and perform image reconstruction computations, causing a delay in imaging relative to the progress of the therapy.

SUMMARY OF INVENTION

The present invention was developed to solve the conventional problems. It is therefore an object of the invention to enable the processing from the measurement to imaging of radiation to be enhanced in speed generally to a real-time level.

A typical PET system, which will be described in relation to a PET system shown in FIG. 2 according to the present invention, is made up of a PET device 100, a data acquisition unit 200, and an image reconstruction unit 300. The data acquisition unit 200 and the image reconstruction unit 300 are often implemented as separate work stations (WS), but may also be implemented in the same WS. Alternatively, all or some of the functions of the data acquisition unit 200 and the image reconstruction unit 300 may also be implemented on a dedicated board.

The PET device 100 is made up of a detector section 110 for detecting one of annihilation radiations (single measurement); an A/D conversion circuit section 120 to compute and digitize, for output, the information on the detection position, the energy, and the detection time of the detected radiation; and a coincidence circuit section 130 for performing a coincidence determination (coincidence measurement) on a pair of annihilation radiations.

For a typical FDG-PET examination, the entire device provides counting rates of about $10^6$ counts to $10^8$ counts per second for the single measurement, and about $10^5$ counts to $10^7$ counts per second for the coincidence measurement. To examine the whole body, measurements are continued for about 20 minutes.

For the coincidence measurement, as a list mode in which pieces of count data with one count recorded in a size of about 32 bits to 64 bits are listed, the count data is outputted through a data transmission interface (I/F) 140 typically in about a few tens of megabytes.

In the data acquisition unit 200, the list mode data captured through a data reception I/F 210 is stored in a memory 240, or a storage device such as a hard disk, via a memory 220 or a semiconductor memory which allows high-speed data access. Hereafter, the memory 240 will be referred to as the OFF memory. To reconstruct an image, the list mode data will be retrieved from the OFF memory 240 and then sent to the image reconstruction unit 300 through a data transmission I/F 250. Note that the memory 220 which temporarily saves the list mode data may be provided as required.

FIG. 2 shows the configuration of a PET system according to the present invention. To prevent a delay in imaging or displaying of images due to concentrated load on the data transmission and the image reconstruction processing in the case of high counting rates, the data acquisition unit 200 is provided with an additional determination processing section 230 which includes a ROM and a CPU for performing determination processing on the list mode data retrieved from the memory 220. More specifically, the determination processing section 230 instantly sends all pieces of list mode data directly to the image reconstruction unit 300 and performs the image reconstruction processing online in real time when the counting rate is so low as not to cause a delay in the imaging with respect to the therapeutic progress. On the other hand, when the counting rate is higher than a certain value thereby causing worry that a delay may occur in imaging, only such an amount of list mode data that can be processed online in real time is transmitted to the image reconstruction unit 300.

Furthermore, the determination processing section 230 saves, in the OFF memory 240 of the data acquisition unit 200, all pieces of list mode data or the list mode data that has not been sent to the image reconstruction unit 300 after the determination processing. This allows for performing additional image reconstruction processing offline after a series of measurements have been completed. Here, the OFF memory 240 does not necessarily have to save data in real time but may do so with a delay. In that case, the data is temporarily saved in a RAM between the determination processing 230 and the OFF memory 240. Furthermore, when not offline but only online processing is performed, the list mode data itself may not be saved.

In the image reconstruction unit 300, after the list mode data is temporarily saved in a memory 320 via a data reception I/F 310, an image reconstruction processing section 330 with a ROM and a CPU performs the image reconstruction processing. To ensure the property of equal quantity between time frames, calibration processing is applied to reconstructed images in a calibration processing section 340 with a ROM and a CPU. More specifically, in the determination processing in the data acquisition unit 200, reconstructed images are weighted according to the ratio of data transmitted as online processed data, i.e., the ratio of the amount of output data from the determination processing section 230 to the data transmission I/F 250 to the amount of input data to the determination processing section 230 in a unit time. Note that the calibration processing may also be performed within the image reconstruction processing section 330. The image on which the calibration processing has been conducted is displayed on an image display device 360 as well as saved in an image memory 350 which is a storage device such as a hard disk.

FIG. 3 illustrates the concept of online processing according to the present invention. Some functions have been omitted. It is assumed that online processing can be performed on N counts per one time frame (e.g., for imaging at time intervals of 30 frames per second, one time frame is 1/30 seconds). The values of N are stored in the determination processing section 230, with N=8 assumed in FIG. 3. Cm is the total number of measured counts within a time frame, and Ce is the number of counts to be retrieved in the determination processing (230) and then sent online to the image reconstruction unit 300. In time frame 1, a total of 7 counts have been measured, but are less than the threshold value (8 counts/frame) of the counting rate, so that all counts are subjected online to the image reconstruction processing. In time frame 2, since a total of 12 counts have been measured, only the first 8 counts are processed online.

Primarily, the number of total counts of the images in time frame 1 and time frame 2 is at a ratio of Cm's, that is, 7:12; however, the Ce ratio leads to 7:8, with the property of equal quantity missing. In this context, for the weighting above, the calibration processing (340) is performed to multiply the pixel value by a weighting coefficient F which is defined by Cm/Ce. The weighting coefficient F is 7/7=1.0 for time frame 1, and 12/8=1.5 for time frame 2.

FIG. 4 shows the operation of offline processing. The list mode data saved in the OFF memory 240 of the data acquisition unit 200 is sequentially transferred to the image reconstruction unit 300 and then subjected to the image reconstruction processing. In the offline processing, since no real time property is required, all pieces of measurement data saved in the OFF memory 240 can be used for reconstruction of images. When all pieces of measurement data are used for image reconstruction, the calibration processing (340) is not required. Note that when a time limit is set for the offline processing, only part of the data saved in the OFF memory 240 can also be used for image reconstruction.

FIG. 5 shows the basic flow of the offline processing (offline mode). In the data acquisition unit 200, all the list mode data is saved (step 230), so that in the offline mode, in each time frame, all pieces of data are used to perform the image reconstruction processing (step 228). In the offline mode, since no real time property is required, the number of repetitions of iterative image reconstructions can be increased to provide images with enhanced accuracy. Here, the step numbers in FIG. 5 are associated with those in the flow of FIG. 6.

The present invention was developed in accordance with the aforementioned findings so as to solve the aforementioned problems of performing real time processing by selecting the number of count data to be used for online imaging computations on the basis of a counting rate of radiation, in imaging on the basis of the list mode data of a list of count data on radiation detected by a nuclear medicine imaging apparatus for measuring radiation in a pulse mode.

Here, when the counting rate of radiation is so low that all pieces of data can be used to process in real time, all the data can be used for online imaging computations, whereas when the counting rate of radiation is so high that all the data cannot be used to process in real time, only an amount of data that can be processed in real time can be used for online imaging computations.

Furthermore, the nuclear medicine imaging apparatus can be a tomography apparatus and the imaging computation can be an image reconstruction computation.

Furthermore, in a processing from the imaging computation to displaying of images, imaging can be performed by multiplying each pixel forming an image by a value of Cm/Ce in each time frame depending on an amount of measured data Cm and an amount of data Ce thereof which has been used in the real time (online) processing.

Furthermore, of the list mode data, data that has not been used in the online processing can be saved in an OFF memory.

Furthermore, of the list mode data, the data that has not been used in the online processing can be saved in the OFF memory, so that the data saved in the OFF memory can be used to perform offline imaging computations.

Alternatively, the list mode data can be saved in the OFF memory, so that the data saved in the OFF memory can be used to perform offline imaging computations.

Alternatively, of the list mode data, at least data that has not been used in the online processing can be saved in the OFF memory, while a real-time image can be saved in an image memory, and the data saved in the OFF memory can be used to modify the real-time image saved in the image memory.

Alternatively, of the list mode data, at least data that has not been used in the online processing can be saved in the OFF memory, while a real-time image can be saved in an image memory, and the image having been subjected to an imaging computation using the data saved in the OFF memory can be added to the real-time image saved in the image memory.

Furthermore, the present invention solve the problems by an imaging system of a nuclear medicine imaging apparatus for imaging from list mode data of a list of count data on radiation detected by the nuclear medicine imaging apparatus for measuring radiation in a pulse mode, the imaging system including means for selecting the number of count data to be used for online imaging computations on the basis of a counting rate of radiation.

Furthermore, the present invention provides a nuclear medicine imaging system including:
a nuclear medicine imaging apparatus for measuring radiation in a pulse mode; and
the above-described imaging system for imaging from the list mode data of a list of count data on radiation detected by the nuclear medicine imaging apparatus.

Furthermore, the invention provides a radiation therapy control system including:
a nuclear medicine imaging apparatus for measuring radiation in a pulse mode;

the above-described imaging system for imaging from the list mode data of a list of count data on radiation detected by the nuclear medicine imaging apparatus; and a device for providing real-time control to a therapy apparatus on the basis of an image obtained by the imaging system.

Here, the image can be an image of radioactive medicine distributed in a body and accumulated at a target, and the control can be irradiation control for tracking, on the basis of the image, the target moving within the body, in synchronization with movement of the target or so as to follow the movement of the target.

Alternatively, the image can be an image correlated with an internal dose distribution, and the control can be irradiation control which allows for irradiating tentatively with a reduced dose of radiation in order to verify from the image whether the irradiations have been carried out as planned, so that if the irradiations are determined not to have been performed as planned, the therapy is stopped or the therapy plan is instantly modified.

According to the present invention, data can be processed in real time with stability in the presence of variations in radioactivity in a field of view, or quickly with a delay kept constant, the delay being caused by a small amount of processing time in a computer or a network.

Accordingly, the present invention is effective for the radiation therapy under the guidance of PET images as well as even for a PET diagnosis with an examination which involves fast pharmacokinetic behaviors in the body and significant variations in radioactivity concentration with time at a region of interest.

The invention is also applicable not only to the PET but also to a measurement system for measuring radiation in a pulse mode.

The data processing can include various types of data processing without being limited to transferring of data, saving of data, and image reconstruction computations.

DESCRIPTION OF EMBODIMENTS

Now, the present invention will be described in more detail with reference to the drawings in accordance with the embodiments.

Figure 1:
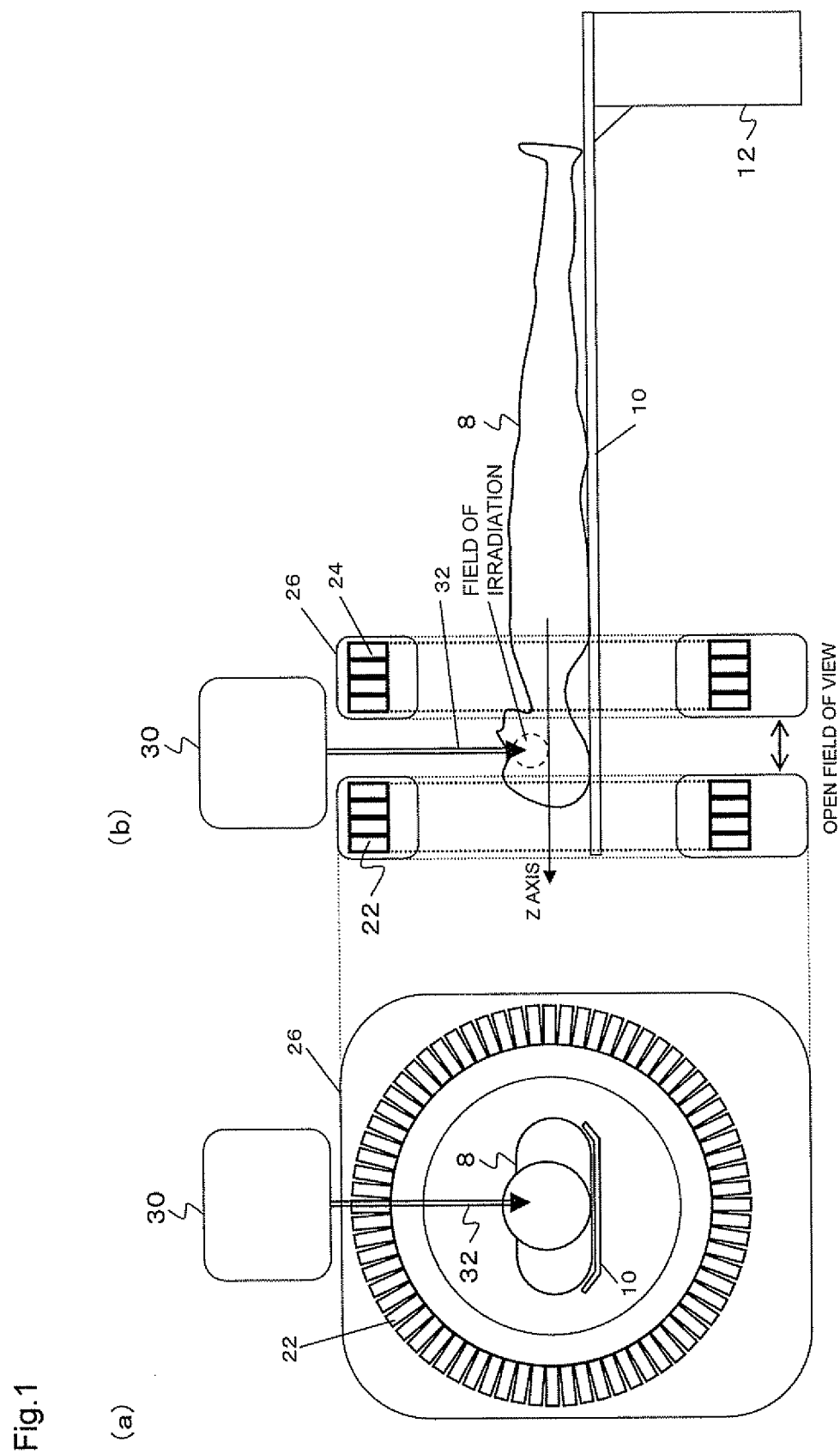
FIGS. 1(a) and (b) are a front view and a side view, respectively, illustrating an open PET device suggested by the inventors.
Figure 2:
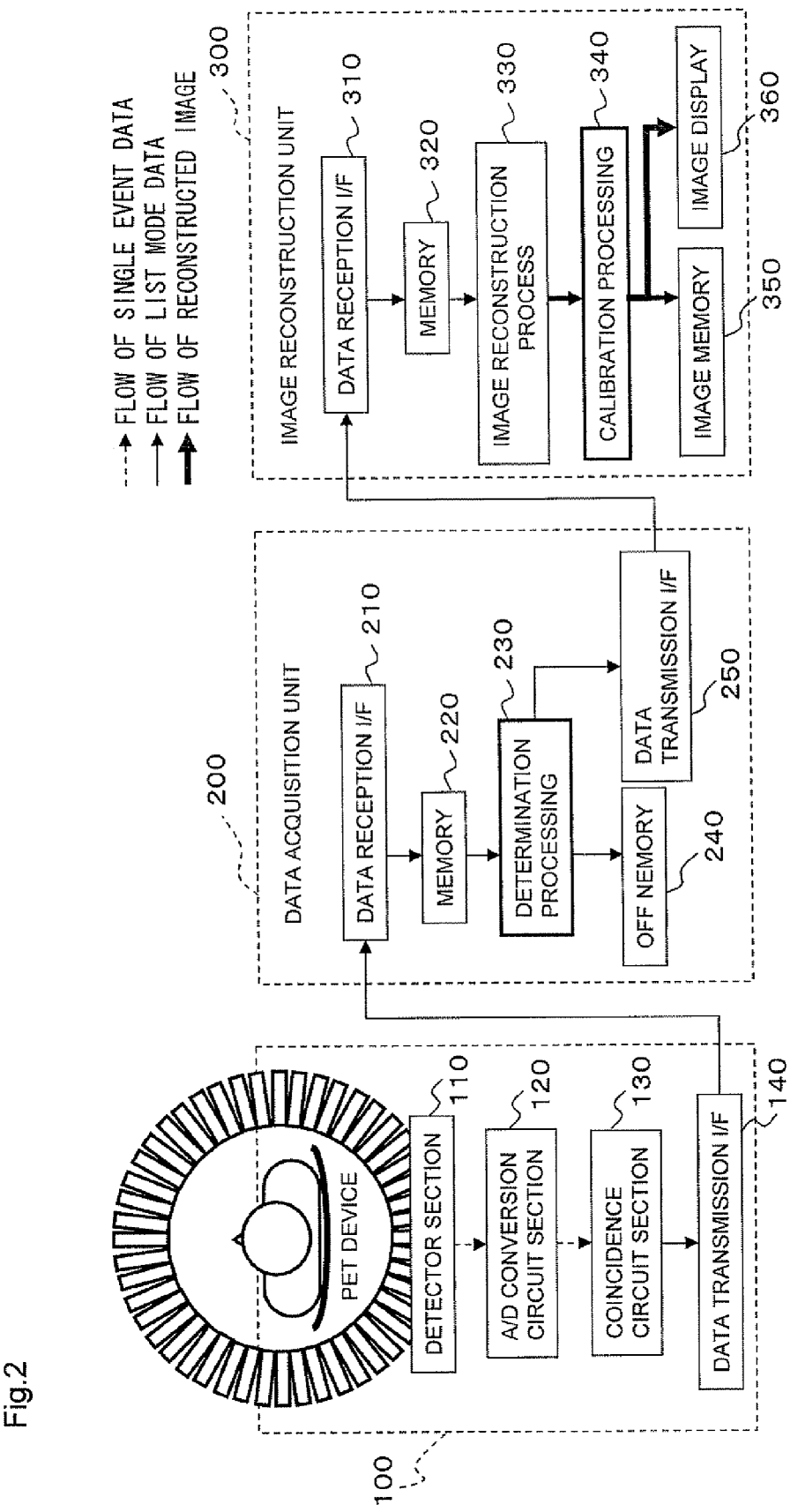
FIG. 2 is a block diagram illustrating the configuration of the entire PET system according to the present invention.
Figure 3:
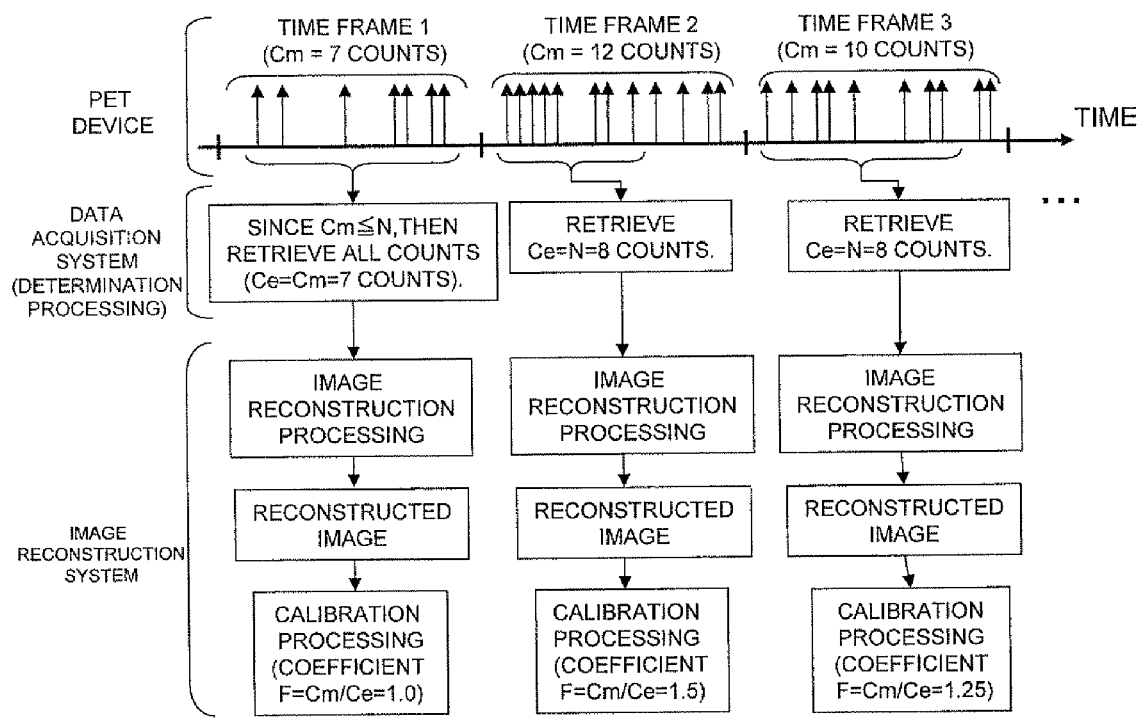
FIG. 3 is a view illustrating an example of the operation of a transfer/save determination according to the present invention.
Figure 4:
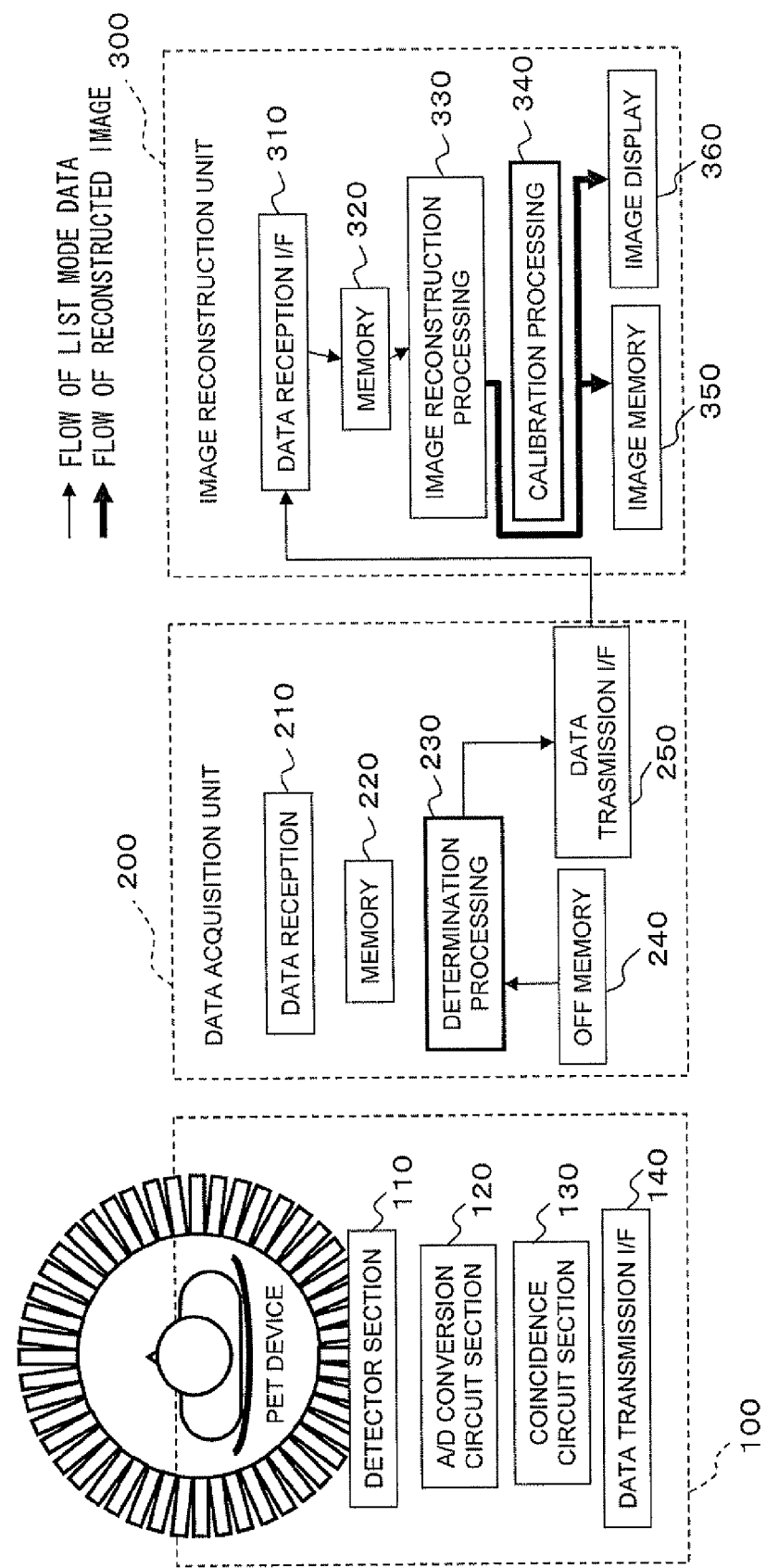
FIG. 4 is a view illustrating an example of the operation of offline processing according to the present invention.
Figure 5:
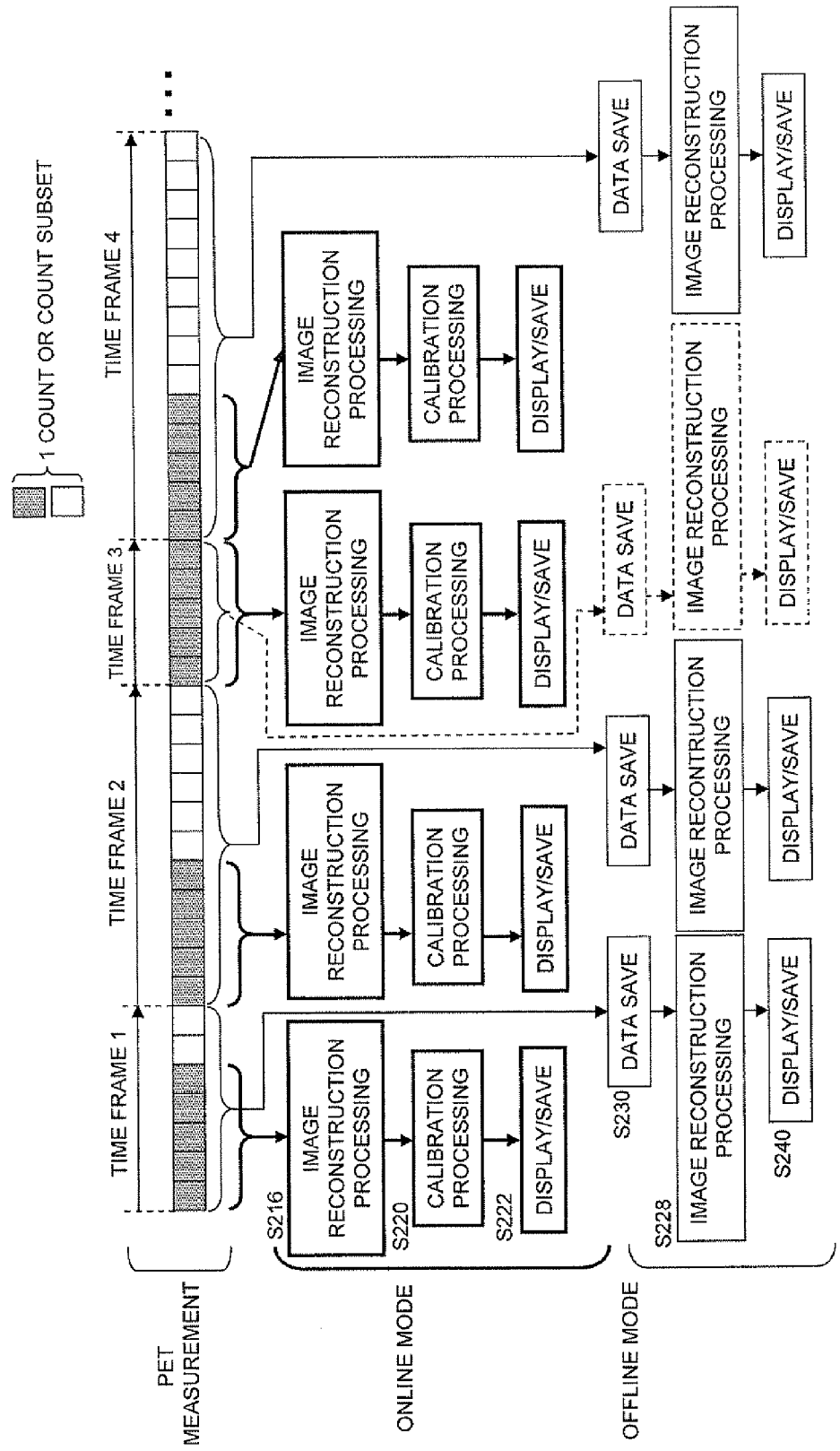
FIG. 5 is a view illustrating the flow of offline processing according to the present invention.
Figure 6:
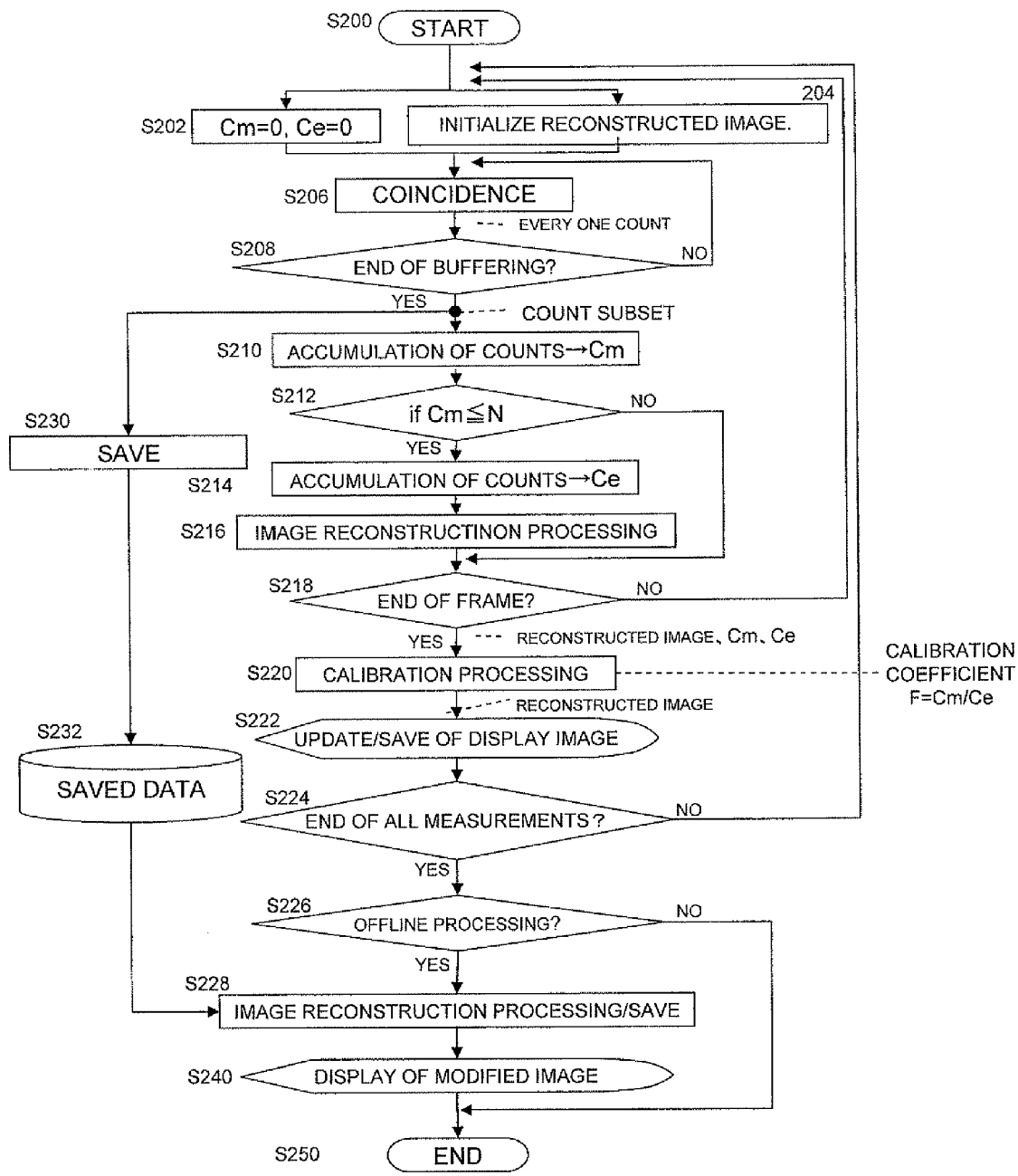
FIG. 6 is a flowchart showing the operation of a first embodiment according to the present invention.

FIG. 6 is a flowchart showing the operation of a first embodiment. First, an accumulated count value Cm in a time frame and an accumulated count value Ce retrieved for online processing in the determination processing section 230 are reset (step 202). At the same time, in the image reconstruction unit 300, a reconstructed image is also reset (step 204).

When a PET measurement is started, a pair of annihilation radiations are subjected to coincidence measurements in the PET device 100 so as to obtain one count (step 206). The data can be transferred from the PET device 100 to the data acquisition unit 200 for every count; however, considering the efficiency of transfer processing, it is desirable to accumulate and buffer counts in the PET device 100 so as to transfer the counts as a count subset to the data acquisition unit 200 (step 208). This buffering is determined to be completed when either the pre-specified number of counts or the pre-specified accumulation time is first exceeded, and then the accumulated count subset is transferred. The accumulation time specified in buffering conditions has to be set so as to be shorter than the time frame of a PET image. By way of example, for the time frame of a PET image of $1/10$ seconds (i.e., 10 frames/sec), the accumulation time is $1/100$ seconds.

In the data acquisition unit 200, the data is successively saved in the OFF memory 240 (step 230). During this processing, the number of counts transferred is accumulated in Cm (step 210). Until Cm exceeds a specified value N, it is determined that real time processing is possible (step 212). The data is transferred to the image reconstruction unit 300, so that the data acquisition unit 200 or the image reconstruction unit 300 accumulates the number of counts Ce sent online for image reconstruction processing (step 214). Then, the image reconstruction processing is performed (step 216).

The specified value N of the number of counts may be pre-set or automatically determined by examining whether images are delivered in real time, i.e., without a delay relative to the time frame, in response to the output rate of the image reconstruction processing (step 216). In this case, as required, the specified value N can be varied temporally. More specifically, there may be a case where when another task occurs in the image reconstruction unit with degradation in throughput halfway through the task, the specified value N is reduced in response to the degradation. When Cm has exceeded the specified value N, no data is transmitted to the image reconstruction unit 300.

When the time frame is ended (step 218), the calibration processing (step 220) is performed to multiply each pixel value of a reconstructed image by Cm/Ce. Then, one frame of display image of the reconstructed image having been subjected to the calibration processing is updated and saved in the image memory 350 (step 222), and this will be repeated for all the measurements (step 224). Assuming that the entire measurement time for the PET is 60 minutes and the time frame is $1/10$ seconds, the aforementioned processing will be repeated 36,000 times. As a result, it is achieved to display images in real time.

When all measurements are ended, the processing can be ended as it is; or the image reconstruction processing (step 228) can be performed to modify the image saved in the image memory 350, using the saved data (step 232) that has been saved in the OFF memory 240, and the processing can then be ended.

Figure 7:
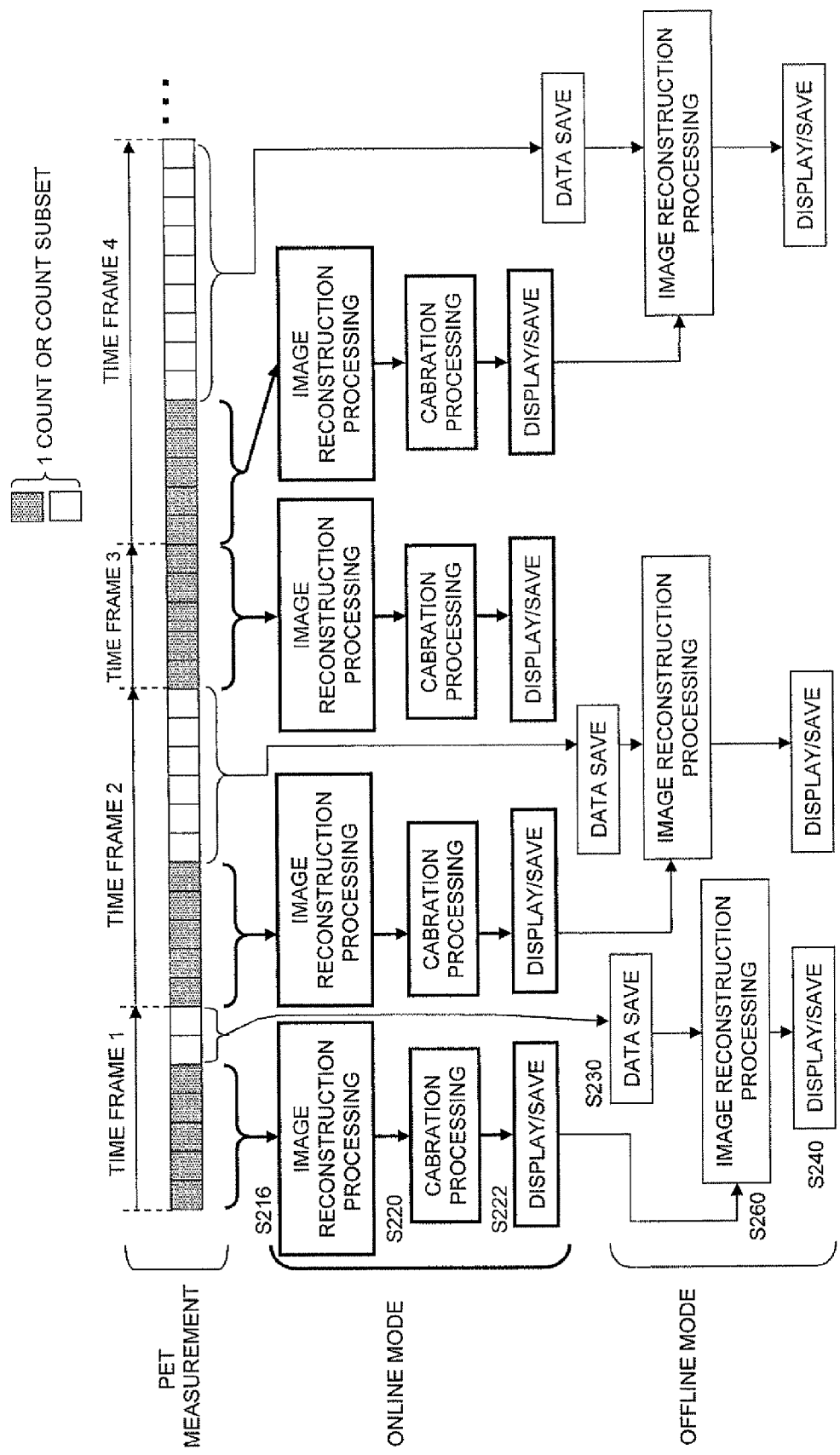
FIG. 7 is a view illustrating a second embodiment for providing an enhanced efficiency to offline processing.

FIG. 7 shows a second embodiment for enhancing the efficiency of computation in the offline processing (offline mode). In each time frame, the image reconstruction processing is not started from the beginning but, as shown in time frames 1, 2, and 4, the reconstructed image in the online mode is based to perform the image reconstruction processing using only the data that was not used in the online processing (step 260). In this case, the calibration processing (step 222) applied in the online mode would cause the property of equal quantity to be compromised in the offline mode. Accordingly, in the image reconstruction processing (step 260), for example, each pixel of a reconstructed image in the online mode has to be multiplied by the reciprocal of the weighting coefficient F applied in the calibration processing (step 222) in order to cancel out the effects of the calibration processing (step 222).

In the present embodiment, since computations require a reduced amount of data (reduced counts), the amount of computation for the image reconstruction processing can be reduced.

In the data acquisition unit 200, only the data that has not been used in the online mode has to be saved. Alternatively, all pieces of list mode data may be saved, and in the offline mode, only the data that has not been used in the online mode can be read out. However, the present embodiment assumes that the image reconstruction processing follows one-pass computation, i.e., no iterative computations, and is thus not intended to perform two or more iterative operations.

Figure 8:
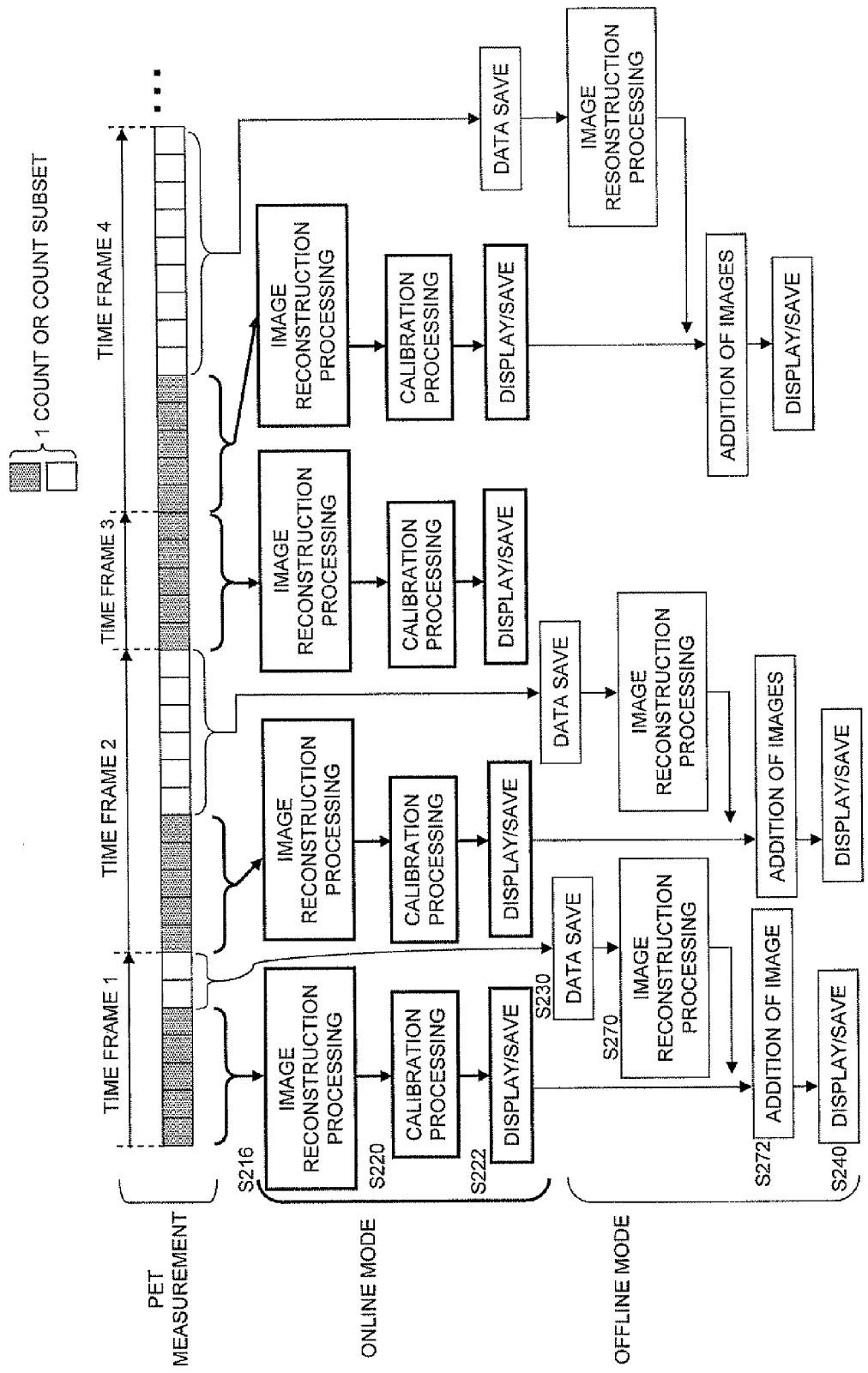
FIG. 8 is a view illustrating a third embodiment according to the present invention.

FIG. 8 shows a third embodiment for enhancing the efficiency of computation in the offline processing (offline mode).

More specifically, as illustrated in time frames 1, 2, and 4, in the offline mode, the image reconstruction processing is performed only on the data that has been saved in the OFF memory 240 and not used in the online processing (step 270). After that, the online-mode reconstructed image saved in the image memory 350 and the offline-mode reconstructed image are simply added to each other (step 272). In the third embodiment, as in the second embodiment, it is necessary to apply the processing for cancelling the effects of the calibration processing (step 222) on the reconstructed image in the online mode. Note that the data to be saved in the OFF memory 240 may be only the data that has not been used in the online processing, or all pieces of data which include both the data that has not been used in the online processing and the data that has been used in the online processing.

Note that the present invention is widely applicable not only to the PET device but also to the nuclear medicine imaging apparatus for measuring radiation in a pulse mode, such as gamma cameras, positron cameras, or single photon emission computed tomography (SPECT) apparatus. Furthermore, the target to be measured may be an animal or plant other than humans.

Figure 9:
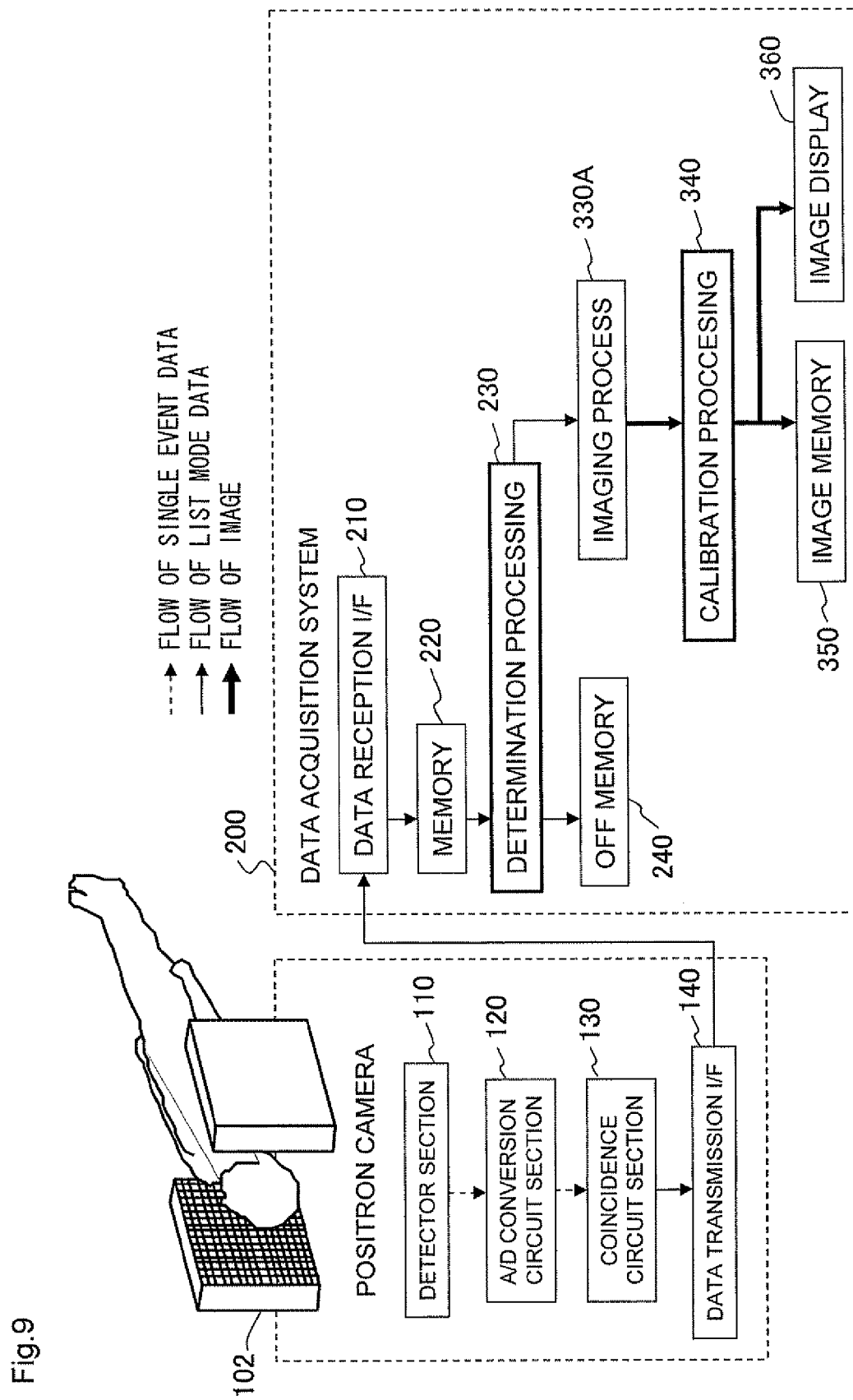
FIG. 9 is a block diagram illustrating the configuration of a fourth embodiment according to the present invention.

FIG. 9 is a block diagram illustrating the configuration of a fourth embodiment of the present invention which is applied not to the PET for tomography apparatus but to a positron camera for performing two-dimensional imaging. Here, the data acquisition unit 200 is integrated with the function of imaging processing. The fundamental structure and operation are the same as those described above, but the image reconstruction processing has been replaced with imaging processing 330A since this embodiment is not intended for tomography.

Note that the memory is means for temporarily or permanently storing digital data that the computer is to process, such as a semiconductor memory, a hard disk, a DVD-ROM, or those that are provided with the function equivalent to the same.

EXAMPLE

The present invention is best available when radiation cancer therapy is to be provided under the guidance of PET images.

Figure 10:
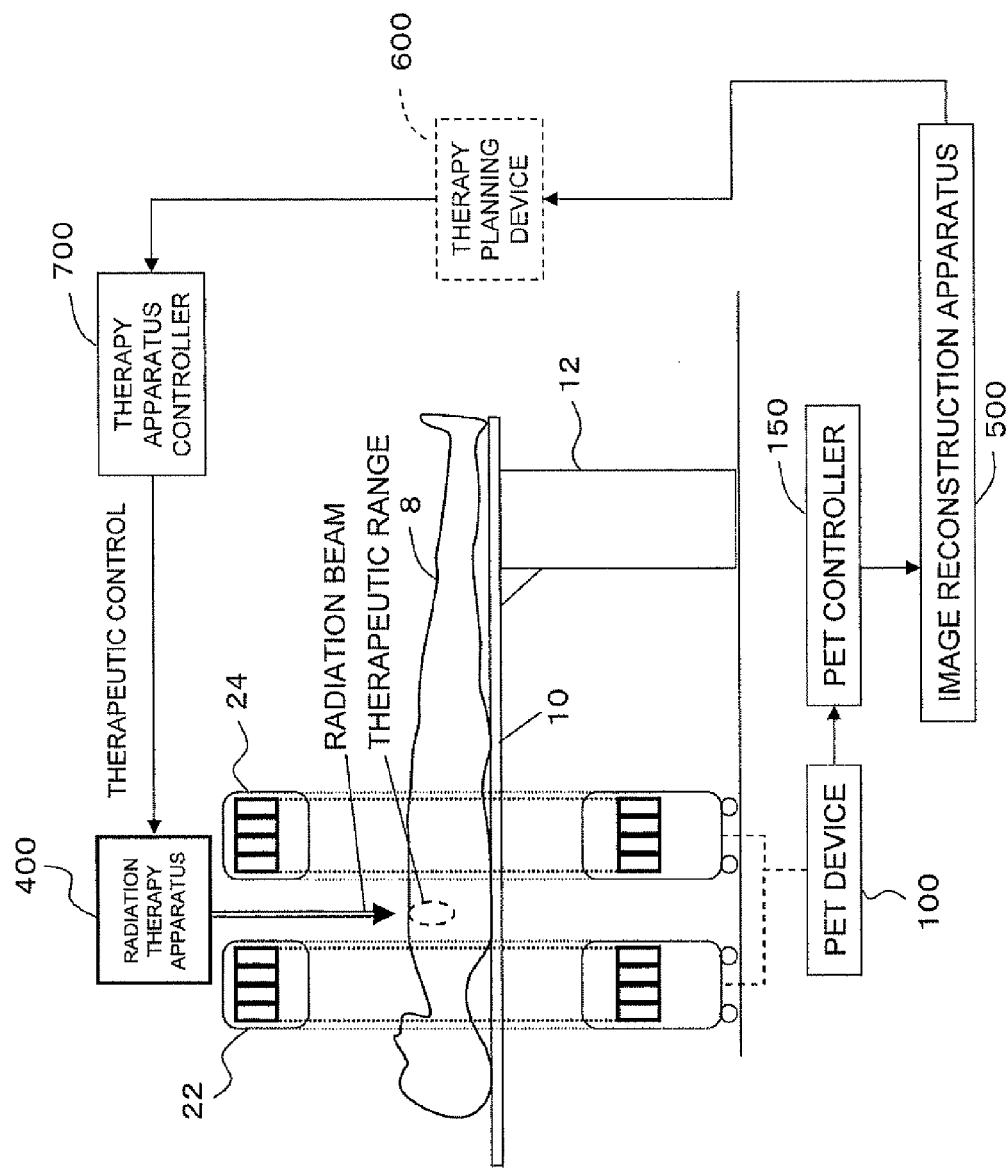
FIG. 10 is a view illustrating an example in which the present invention has been applied to a radiation cancer therapy.

FIG. 10 shows an example in which a radiation (cancer) therapy apparatus 400 is combined with the open PET device 100 to implement a real time image reconstruction system according to the present invention. The figure shows a patient 8, a bed 10, a base 12 of the bed 10, detector rings 22 and 24, a PET controller 150, an image reconstruction apparatus 500 which includes the data acquisition unit 200 and the image reconstruction unit 300, a therapy planning device 600, and a therapy apparatus controller 700.

Using a marker such as fludeoxyglucose (FDG) representative of a PET probe that collects in cancer, only a target such as lung cancer moving within the body can be accurately irradiated with radiation while tracking the target in real time on the PET images.

Figure 11:
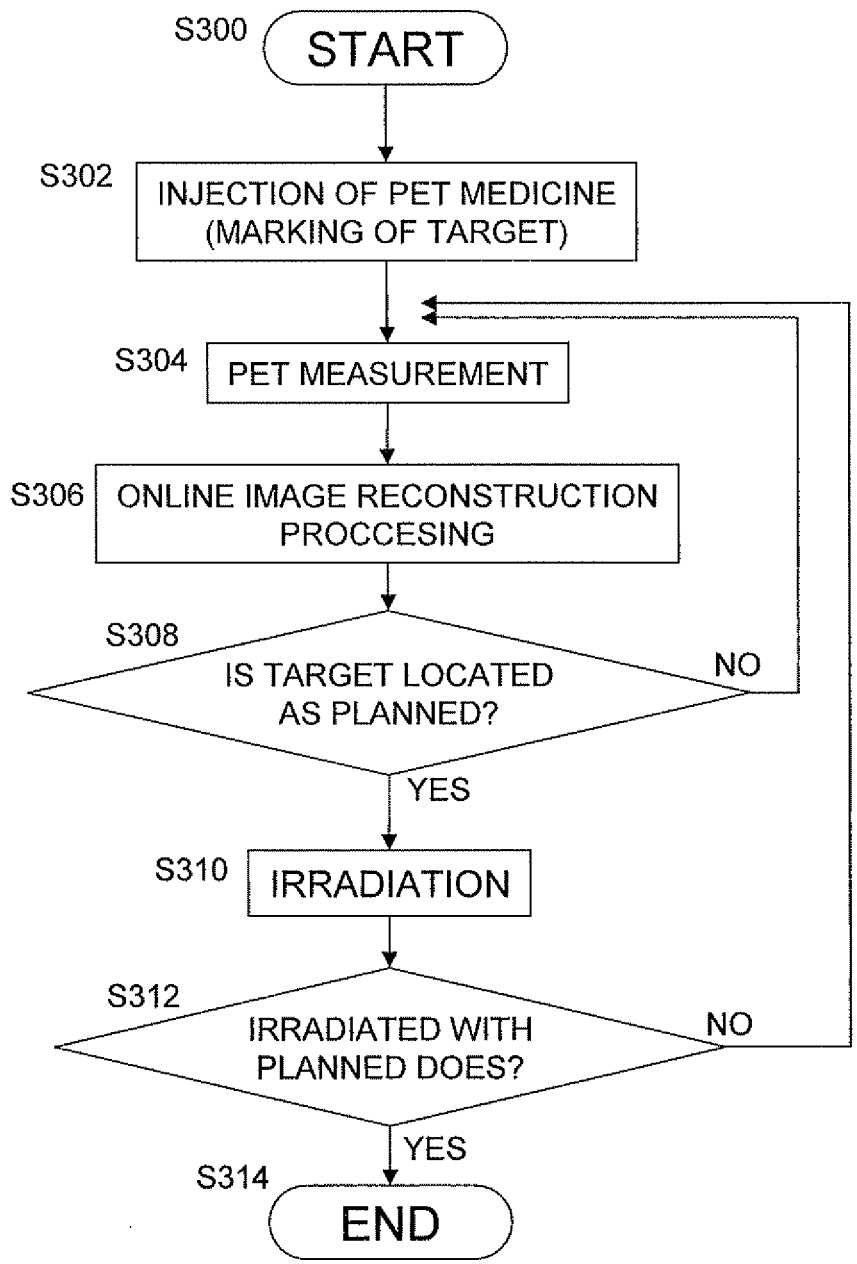
FIG. 11 is a flowchart showing an example of the procedure for following a moving target so as to irradiate the target with radiation.
Figure 12:
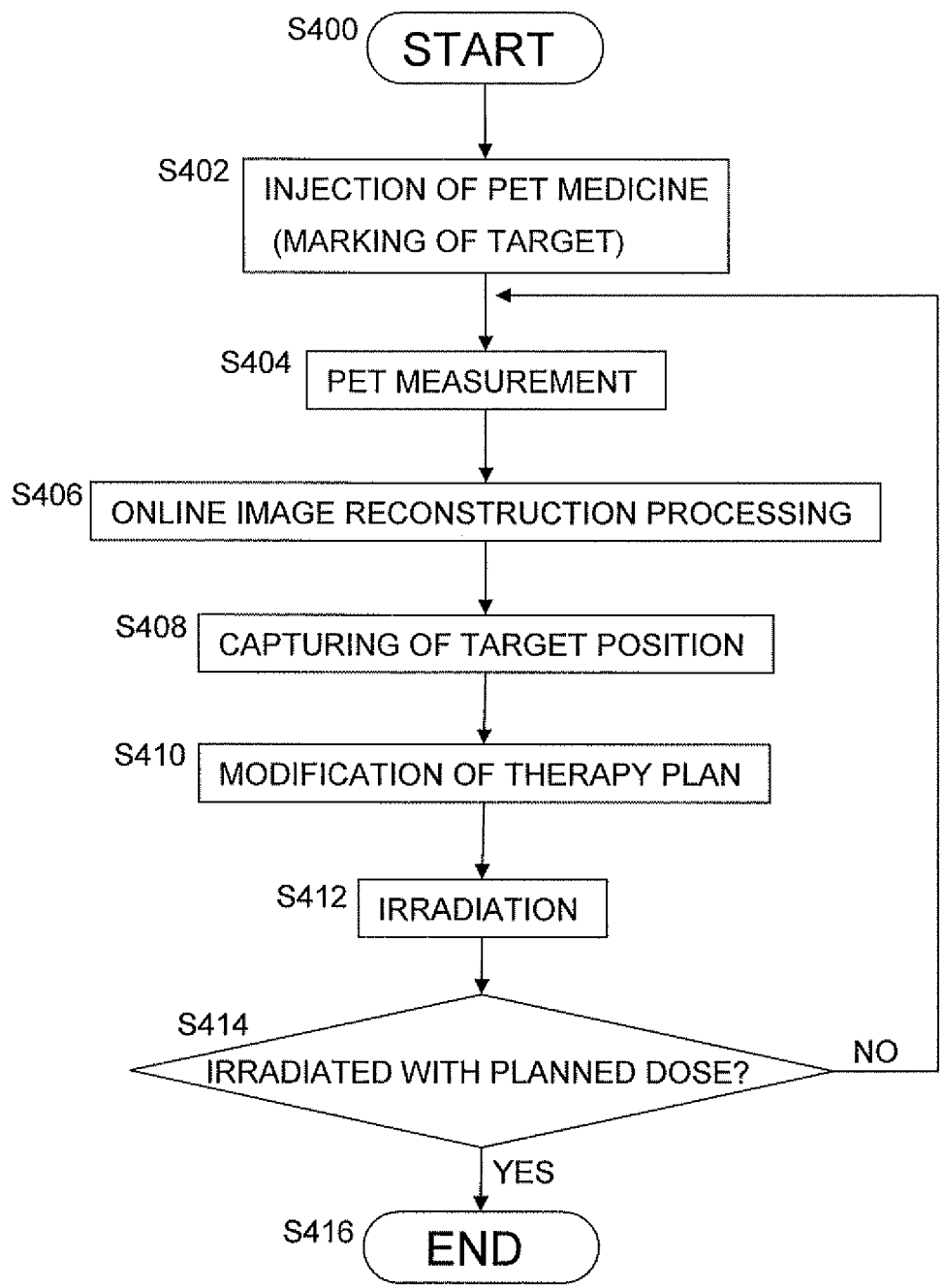
FIG. 12 is a flowchart showing another example of the procedure.

FIGS. 11 and 12 show the specific procedures.

FIG. 11 shows a method for performing irradiations (step 310) only at the instant at which the target has come to the planned position (step 308) on the PET images (step 306) without modifying the therapy plan itself. The determination of whether the target is at the planned position (step 308) can be made by the operator while viewing the PET images, or alternatively, may be automatically conducted in the therapy apparatus controller 700.

FIG. 12 shows a method for performing irradiations by instantly capturing (step 408) the target position from the PET images (step 406) and re-computing the irradiation position in the therapy planning device 600 without a delay (step 410), thereby following the moving target.

Figure 13:
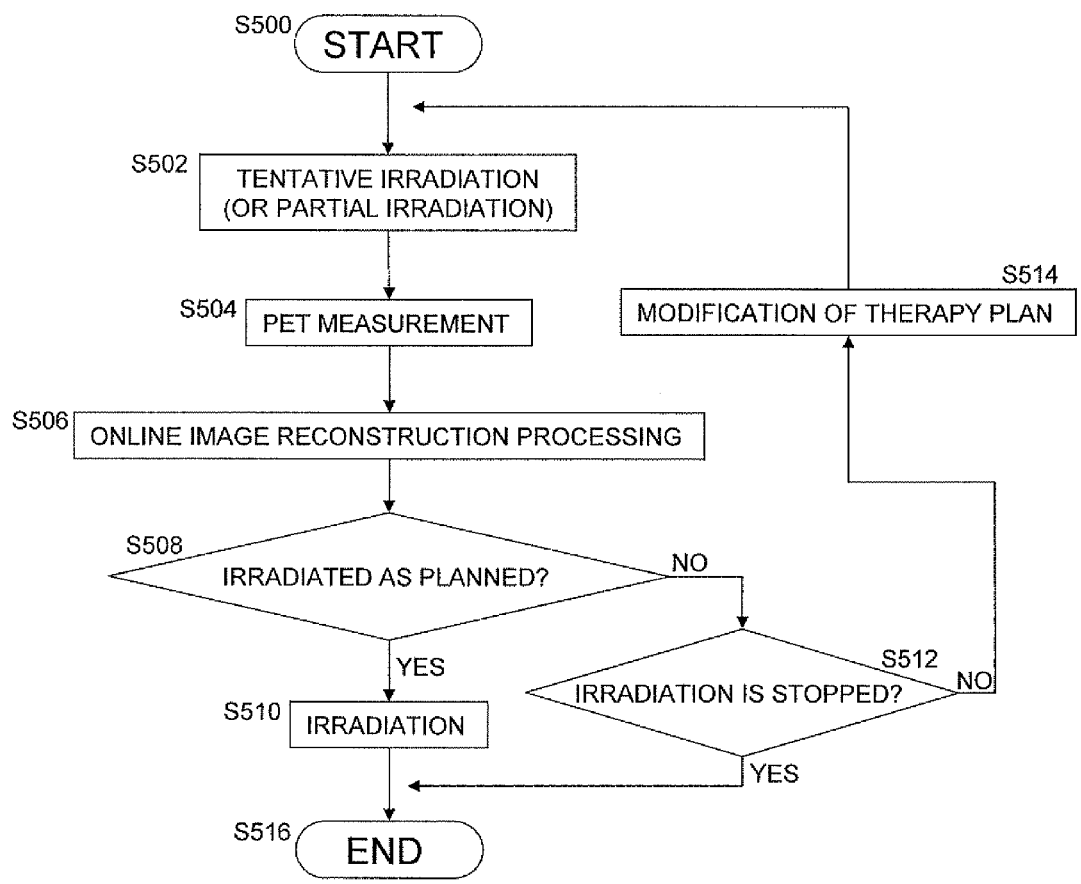
FIG. 13 is a flowchart showing an example which is applied to a particle beam cancer therapy.

FIG. 13 shows an example in which the present invention is applied to the particle beam cancer therapy. The particle beam cancer therapy for concentratedly irradiating a cancer portion with heavy particle beams or proton beams has gained great attention as a method for providing outstanding therapeutic effects and irradiating affected areas with sharply focused beams. Irradiations are performed by providing precise control to the direction and the dose of beams according to the therapy plan that has been carefully computed on the basis of separately captured X-ray CT images. However, under current circumstances, it is difficult to accurately confirm whether the irradiations have been performed following the therapy plan, so that even when the field of irradiation is shifted due to the displacement of the patient, this would not be easy to detect. In this context, a method for monitoring the field of irradiation of particle beams in real time using a PET technique has gained attention. This method employs no PET medicine but the PET principle to image the annihilation radiation resulting from the incident nucleus fragmentation reaction and the target nucleus fragmentation reaction which are caused by irradiation with beams. Great promise is expected for this method because the position of occurrence of the annihilation radiation is strongly correlated with the dose distribution of irradiation beams, and thus this would allow therapy monitoring to be made possible.

In FIG. 13, for example, the process tentatively irradiates the affected area with a therapy dose at an intensity reduced to $\frac{1}{10}$ (step 502) and images the dose distribution in the patient body by PET measurements (step 504) and the online image reconstruction processing (step 506) according to the present invention, so that whether the irradiations have been provided as planned is instantly determined by comparing the resulting image with the PET images that are computed from the therapy plan or by means such as by simulation on the basis of the therapy plan (step 508). When it is determined that the irradiations have not been provided as planned, the therapy itself is stopped ("Yes" as the determination result in step 512) or the therapy plan itself is instantly modified depending on the level of deviation (step 514) and then test irradiations are conducted again for confirmation (step 502).

INDUSTRIAL APPLICABILITY

The present invention can accelerate, substantially to the real time level, the processing from the measurement to imaging of radiation in gamma cameras, positron cameras, single photon emission computed tomography (SPECT) apparatus, or positron emission tomography (PET) device, and thus provide a very high applicability to industry.

REFERENCE SIGNS LIST

8 . . . patient
10 . . . bed
100 . . . PET device
110 . . . detector section
150 . . . PET controller
200 . . . data acquisition unit
220, 320 . . . memory
230 . . . determination processing section
240 . . . OFF memory
300 . . . image reconstruction unit
330 . . . image reconstruction processing section
340 . . . calibration processing section
350 . . . image memory
360 . . . image display section
400 . . . radiation therapy apparatus
500 . . . image reconstruction apparatus
600 . . . therapy planning device
700 . . . therapy apparatus controller

The invention claimed is:

1. An imaging method of a nuclear medicine imaging apparatus for imaging from list mode data of a list of count data on radiation detected by the nuclear medicine imaging apparatus for measuring radiation in a pulse mode,
the imaging method comprising selecting the number of count data to be used for online imaging computations on the basis of a counting rate of radiation,
wherein when the counting rate of radiation is so low that all pieces of data can be used to process in real time, all the data is used for online imaging computations, and
wherein when the counting rate of radiation is so high that all the data cannot be used to process in real time, only an amount of data that can be processed in real time is used for online imaging computations.

2. The imaging method of a nuclear medicine imaging apparatus according to claim 1, wherein the nuclear medicine imaging apparatus is a tomography apparatus and the imaging computation is an image reconstruction computation.

3. The imaging method of a nuclear medicine imaging apparatus according to claim 1, wherein, of the list mode data, data that has not been used in the online processing is saved in an OFF memory.

4. The imaging method of a nuclear medicine imaging apparatus according to claim 3, wherein the data saved in the OFF memory is used to perform offline imaging computations.

5. The imaging method of a nuclear medicine imaging apparatus according to claim 1, wherein the list mode data is saved in an OFF memory, so that the data saved in the OFF memory is used to perform offline imaging computations.

6. The imaging method of a nuclear medicine imaging apparatus according to claim 1, wherein, of the list mode data, at least data that has not been used in the online processing is saved in an OFF memory, while a real-time image is saved in an image memory, and the data saved in the OFF memory is used to modify the real-time image saved in the image memory.

7. The imaging method of a nuclear medicine imaging apparatus according to claim 1, wherein, of the list mode data, at least data that has not been used in the online processing is saved in an OFF memory, while a real-time image is saved in an image memory, and the image having been subjected to an imaging computation using the data saved in the OFF memory is added to the real-time image saved in the image memory.

8. An imaging method of a nuclear medicine imaging apparatus for imaging from list mode data of a list of count data on radiation detected by the nuclear medicine imaging apparatus for measuring radiation in a pulse mode,
the imaging method comprising selecting the number of count data to be used for online imaging computations on the basis of a counting rate of radiation,
wherein in a processing from the imaging computation to displaying of images, imaging is performed by multiplying each pixel forming an image by a value of Cm/Ce in each time frame depending on an amount of measured data Cm and an amount of data Ce thereof which has been used in the real time (online) processing.

9. An imaging system of a nuclear medicine imaging apparatus for imaging from list mode data of a list of count data on radiation detected by the nuclear medicine imaging apparatus for measuring radiation in a pulse mode,
the imaging system comprising means for selecting the number of count data to be used for online imaging computations on the basis of a counting rate of radiation,
wherein when the counting rate of radiation is so low that all pieces of data can be used to process in real time, all the data is used for online imaging computations, and
wherein when the counting rate of radiation is so high that all the data cannot be used to process in real time, only an amount of data that can be processed in real time is used for online imaging computations.

10. The imaging system of a nuclear medicine imaging apparatus according to claim 9, wherein the nuclear medicine imaging apparatus is a tomography apparatus and the imaging computation is an image reconstruction computation.

11. The imaging system of a nuclear medicine imaging apparatus according to claim 9, comprising an OFF memory in which, of the list mode data, data that has not been used in the online processing is saved.

12. The imaging system of a nuclear medicine imaging apparatus according to claim 11, wherein the data saved in the OFF memory is used to perform offline imaging computations.

13. The imaging system of a nuclear medicine imaging apparatus according to claim 9, comprising an OFF memory in which the list mode data is saved, so that the data saved in the OFF memory is used to perform offline imaging computations.

14. The imaging system of a nuclear medicine imaging apparatus according to claim 9, comprising an OFF memory in which, of the list mode data, at least data that has not been used in the online processing is saved, and an image memory in which a real-time image is saved, and wherein the data saved in the OFF memory is used to modify the real-time image saved in the image memory.

15. The imaging system of a nuclear medicine imaging apparatus according to claim 9, comprising an OFF memory in which, of the list mode data, at least data that has not been used in the online processing is saved, and an image memory in which a real-time image is saved, and wherein the image having been subjected to an imaging computation using the data saved in the OFF memory is added to the real-time image saved in the image memory.

16. A nuclear medicine imaging system, comprising:
a nuclear medicine imaging apparatus for measuring radiation in a pulse mode; and
the imaging system according to claim 9, for imaging from the list mode data of a list of count data on radiation detected by the nuclear medicine imaging apparatus.

17. A radiation therapy control system comprising:
a nuclear medicine imaging apparatus for measuring radiation in a pulse mode;
the imaging system according to claim 9, for imaging from the list mode data of a list of count data on radiation detected by the nuclear medicine imaging apparatus; and
a device for providing real-time control to a therapy apparatus on the basis of an image obtained by the imaging system.

18. The radiation therapy control system according to claim 17, wherein the image is an image of radioactive medicine distributed in a body and accumulated at a target, and the control is irradiation control for tracking, on the basis of the image, the target moving within the body, in synchronization with movement of the target or so as to follow the movement of the target.

19. The radiation therapy control system according to claim 17, wherein the image is an image correlated with an internal dose distribution, and the control is irradiation control which allows for irradiating tentatively with a reduced dose of radiation in order to verify from the image whether the irradiations have been carried out as planned, so that if the irradiations are determined not to have been performed as planned, the therapy is stopped or the therapy plan is instantly modified.

20. An imaging system of a nuclear medicine imaging apparatus for imaging from list mode data of a list of count data on radiation detected by the nuclear medicine imaging apparatus for measuring radiation in a pulse mode,
the imaging system comprising means for selecting the number of count data to be used for online imaging computations on the basis of a counting rate of radiation,
wherein in a processing from the imaging computation to displaying of images, imaging is performed by multiplying each pixel forming an image by a value of $C_m/C_e$ in each time frame depending on an amount of measured data $C_m$ and an amount of data $C_e$ thereof which has been used in the real time processing.

\* \* \* \* \*